United States Patent
Sullivan

(10) Patent No.: US 7,033,325 B1
(45) Date of Patent: *Apr. 25, 2006

(54) GUIDEWIRE WITH MULTIPLE RADIOPAQUE MARKER SECTIONS

(75) Inventor: Daniel J. Sullivan, Plymouth, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 878 days.

This patent is subject to a terminal disclaimer.

(21) Appl. No.: 09/699,626

(22) Filed: Oct. 30, 2000

Related U.S. Application Data

(63) Continuation of application No. 08/673,674, filed on Jun. 26, 1996, now Pat. No. 6,179,788, which is a continuation of application No. 07/969,047, filed on Oct. 30, 1992, now abandoned, which is a continuation of application No. 07/452,710, filed on Dec. 19, 1989, now Pat. No. 5,209,730.

(51) Int. Cl.
*A61B 5/00* (2006.01)
*A61M 25/00* (2006.01)
*A61B 5/103* (2006.01)

(52) U.S. Cl. ............ 600/585; 604/96.01; 600/434

(58) Field of Classification Search ........ 600/433–435, 600/585; 604/523–532, 96.01; 33/511, 33/512; 606/194
See application file for complete search history.

(56) References Cited

U.S. PATENT DOCUMENTS

| | | | |
|---|---|---|---|
| 3,605,750 A | 9/1971 | Sheridan et al. | |
| 3,847,157 A | 11/1974 | Caillouette et al. | |
| 4,027,659 A | 6/1977 | Slingluff | |
| 4,279,252 A | 7/1981 | Martin | |
| 4,411,055 A | * 10/1983 | Simpson et al. | 29/447 |
| 4,469,483 A | 9/1984 | Becker et al. | |
| 4,538,622 A | 9/1985 | Samson et al. | |
| 4,554,929 A | 11/1985 | Samson et al. | |
| 4,577,637 A | 3/1986 | Mueller, Jr. | |
| 4,641,654 A | 2/1987 | Samson et al. | |
| 4,657,024 A | 4/1987 | Coneys | |
| 4,669,465 A | * 6/1987 | Moore et al. | 606/7 |
| 4,671,291 A | 6/1987 | Wilson | |
| 4,763,647 A | * 8/1988 | Gambale | 600/434 |

(Continued)

FOREIGN PATENT DOCUMENTS

EP      0 054 609 A2     7/1981

(Continued)

*Primary Examiner*—Charles Marmor
(74) *Attorney, Agent, or Firm*—Crompton, Seager & Tufte, LLC

(57) ABSTRACT

An over-the-wire balloon catheter has a radiopaque marker thereon at a known distance from a distal end of the catheter. An elongated flexible guide wire has a plurality of longitudinally spaced radiopaque markers on a distal portion thereof, with adjacent markers on the guide wire being longitudinally spaced at a distance equal to the known distance between the distal end of the catheter and its radiopaque marker. The guide wire is advanced through an artery until one of its markers is positioned at a desired location relative to a stenosis. Subsequently, the balloon catheter is advanced over the guide wire until the radiopaque marker of the catheter is in a predetermined position relationship to the radiopaque marker of the guide wire which has aligned on the stenosis. The cooperating radiopaque markers of the guide wire and catheter thus allow the balloon member of the catheter to be positioned relative to the stenosis in a timely fashion without the need to constantly inject fluoroscopic dye to view the stenosis.

2 Claims, 1 Drawing Sheet

U.S. PATENT DOCUMENTS

| | | | |
|---|---|---|---|
| 4,796,637 A | 1/1989 | Mascuch et al. | |
| 4,821,722 A | 4/1989 | Miller et al. | |
| 4,838,879 A | 6/1989 | Tanabe et al. | |
| 4,922,924 A * | 5/1990 | Gambale et al. | 600/585 |
| 4,946,466 A | 8/1990 | Pinchuk et al. | |
| 5,007,434 A * | 4/1991 | Doyle et al. | 600/585 |
| 5,021,043 A | 6/1991 | Becker | |
| 5,063,935 A | 11/1991 | Gambale | 128/657 |
| 5,084,022 A | 1/1992 | Claude | 604/164 |
| 5,144,959 A | 9/1992 | Gambale et al. | 128/772 |
| 5,147,317 A | 9/1992 | Shank et al. | |
| 5,154,179 A | 10/1992 | Ratner | |
| 5,169,386 A | 12/1992 | Becker et al. | |
| 5,174,302 A | 12/1992 | Palmer | |
| 5,209,730 A | 5/1993 | Sullivan | |
| 5,259,393 A | 11/1993 | Corso, Jr. et al. | 128/772 |
| 5,267,574 A | 12/1993 | Viera et al. | 128/772 |
| 5,345,945 A | 9/1994 | Hodgson et al. | 128/772 |
| 5,353,808 A | 10/1994 | Viera | 128/772 |
| 5,365,942 A | 11/1994 | Shank | 128/772 |
| 5,406,960 A | 4/1995 | Corso, Jr. | 128/772 |
| 5,465,732 A | 11/1995 | Abele | 128/772 |
| 5,479,938 A | 1/1996 | Weier | 128/772 |
| 5,498,250 A | 3/1996 | Prather | 604/280 |
| 5,551,444 A | 9/1996 | Finlayson | 128/772 |
| 5,606,981 A | 3/1997 | Tartacower et al. | 128/772 |
| 5,673,707 A | 10/1997 | Chandrasekaran | 128/772 |
| 5,836,892 A | 11/1998 | Lorenzo | 600/585 |
| 5,957,865 A | 9/1999 | Backman et al. | 600/585 |
| 5,984,877 A | 11/1999 | Fleischhacker, Jr. | 600/585 |
| 6,019,736 A | 2/2000 | Avellanet et al. | 600/585 |
| 6,027,461 A | 2/2000 | Walker et al. | 600/585 |
| 6,042,876 A | 3/2000 | Deem | 427/2.28 |
| 6,132,388 A | 10/2000 | Fleming et al. | 600/585 |
| 6,139,511 A * | 10/2000 | Huter et al. | 600/585 |
| 6,179,788 B1 | 1/2001 | Sullivan | |

FOREIGN PATENT DOCUMENTS

| | | |
|---|---|---|
| EP | 0 749 334 B1 | 3/1995 |
| EP | 0 771 572 A1 | 10/1996 |
| WO | WO 86/06285 | 11/1986 |
| WO | WO 95/24237 | 3/1995 |

* cited by examiner

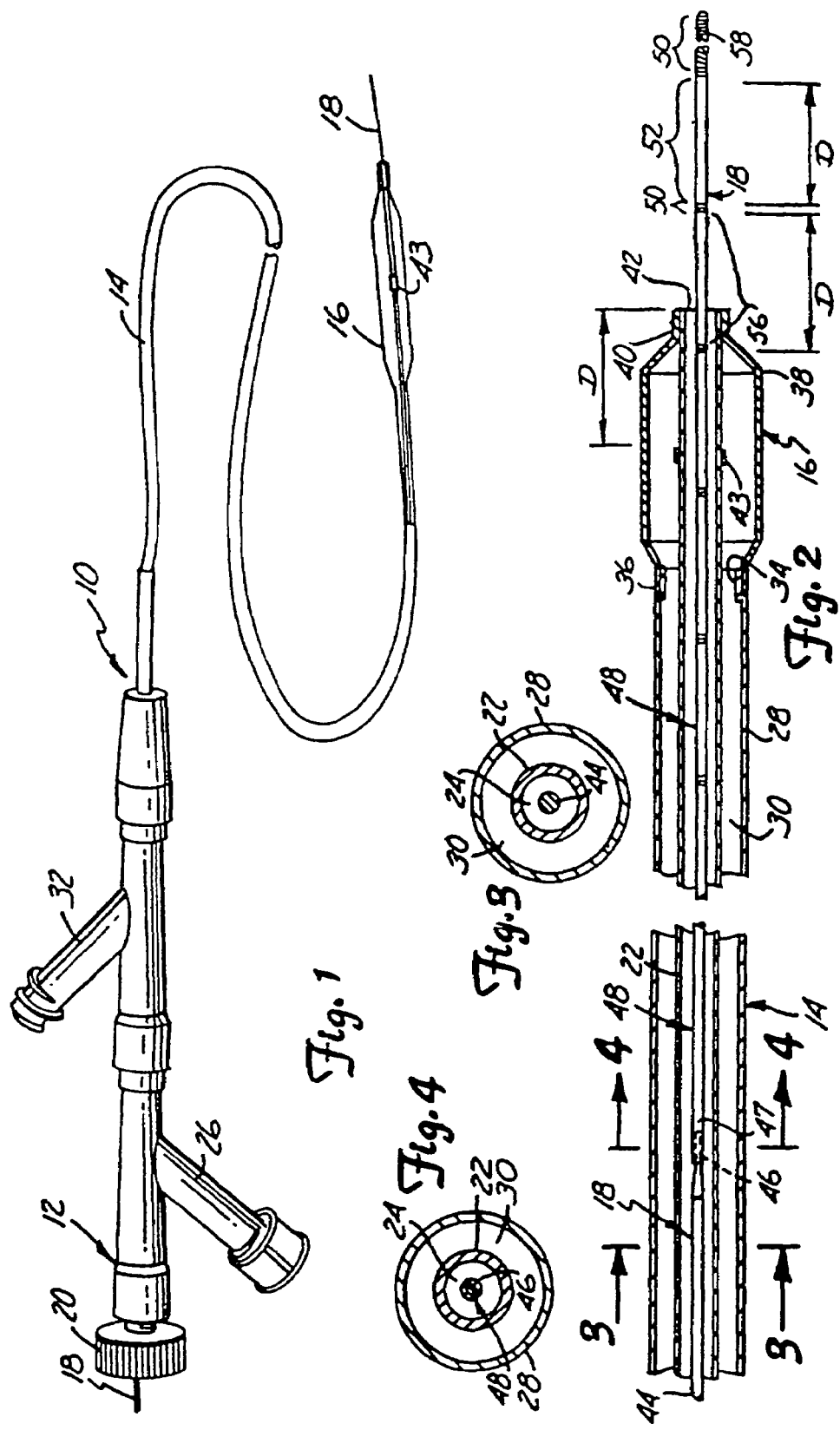

GUIDEWIRE WITH MULTIPLE RADIOPAQUE MARKER SECTIONS

This application is a continuation of application Ser. No. 08/673,674, filed Jun. 26, 1996, now U.S. Pat. No. 6,179,788; which in turn is a continuation of application Ser. No. 07/969,047, filed Oct. 30, 1992, now abandoned; which in turn is a continuation of application Ser. No. 07/452,710, filed Dec. 19, 1989, now U.S. Pat. No. 5,209,730.

BACKGROUND OF THE INVENTION

1. Field of the Invention

The present invention relates to the field of angioplasty and in particular, to new and improved catheters for performing balloon angioplasty procedures on blood vessels.

2. Description of the Prior Art

Angioplasty has gained wide acceptance in recent years as an efficient and effective method for treating vascular diseases. Angioplasty is widely used in the treatment of stenosis within the coronary arteries, although it has been used for the treatment of stenosis in other areas of the vascular system.

The most widely used method of angioplasty makes use of a dilatation catheter which has an inflatable balloon member at a distal end and an inner lumen for acceptance of a guide wire (commonly called an "over-the-wire catheter"). The guide wire is typically about 175 cm in length, and is threaded through the vascular system by tracking radiopaque markers contained at a distal tip of the guide wire, which are monitored on an x-ray fluoroscope. Once the guide wire is positioned, the dilatation catheter is pushed along the guide wire until its balloon member is across the stenosis. The balloon member is subsequently inflated with liquid, exerting pressure radially and outwardly against the stenosis, causing the artery wall to starch and re-establishing an acceptable blood flow through the artery.

An area of stenosis is normally transparent to x-ray fluoroscope viewing, but can be seen by a periodic injection of dye into the artery. This periodic injection allows a limited time fluoroscopic viewing of the restricted artery flow caused by the stenosis, allowing the guide wire to be positioned across the stenosis and into a distal artery, which provides support for the dilatation catheter. However, because dye injections cause surgical complications, physicians derived disfavor injecting additional dye into the artery in order to properly position the balloon member. On the other hand, physicians want to complete the operation as quickly as possible in order to minimise radiation exposure to the patient and staff. Thus, physicians do not want to spend a large amount of time trying to locate the stenosis. Therefore, there is a need for a method to properly mark a stenosis in order to timely position the balloon member without injecting additional dye.

In addition to properly positioning a first balloon member across the stenosis, some surgical procedures require the use of more than one dilatation catheter. For example, the balloon member of the first catheter might have a profile that is too large to fit into the stenosis. Using an extendable or exchange (300 cm in length) guide wire, a physician can exchange the first balloon member with a dilatation catheter having a second balloon member with a smaller profile, while attempting to maintain the guide wire in its position across the stenosis.

A dilatation catheter normally contains one or more markers to allow its balloon member to be located on a fluoroscope. To position the balloon member without the use of additional dye, a method must be used whereby the stenosis can be pinpointed while the stenosis is temporarily displayed. One method is to use a grease pen to mark the location of the stenosis on the screen of the fluoroscope. Another method is to take a picture of the fluoroscope screen while the stenosis can be seen and then use the picture to later position the balloon member across the stenosis.

As can be readily appreciated, these methods of positioning a balloon member are generally time consuming and relatively inaccurate. Also, they require the patient to remain perfectly still in order to have the location marked on the screen correspond to the actual location of the stenosis. Keeping the patient sill is especially difficult when a second dilatation catheter is needed to perform the procedure because of the additional time required to complete the catheter exchange on the guide wire. Therefore, there is a need for an accurate method of positioning a balloon member of an over-the-wire dilatation catheter across a stenosis in a timely fashion and without injecting additional dye to locate the stenosis.

SUMMARY OF THE INVENTION

Unlike previous balloon dilatation catheter system which lack an accurate method and apparatus for marking the location of a stenosis to allow proper placement of a balloon member, the present invention offers the advantage of providing an apparatus and method that allows the stenosis to be pinpointed with respect to a radiopaque marker on a distal portion of a guide wire. Once the location of the stenosis has been established relative to a radiopaque marker carried by the guide wire, the balloon member is placed across the stenosis by aligning the balloon member with respect to the radiopaque marker on the guide wire.

The present invention is an improved apparatus for use in combination with an over-the-wire balloon catheter having a radiopaque marker thereon at a known distance from a distal end of the catheter. An elongated flexible guide wire is provided, and the guide wire has a plurality of radiopaque markers on a distal portion thereof. Adjacent markers on the guide wire are longitudinally spaced at a distance equal to the known distance between a distal end of the catheter and its radiopaque marker.

In a preferred embodiment, the guide wire has a proximal solid wire portion and a distal coil spring portion. A distal radiopaque tip of 1.5 cm is provided on the guide wire, and the rest of the markers on the guide wire are spaced apart 1.5 cm and are each 1 mm in width. The length of the guide wire is preferably 175 cm.

The inventive method of positioning a balloon catheter relative to an artery stenosis begins by advancing the guide wire through the artery and across the stenosis such that a radiopaque marker on the guide wire pinpoints the location of the stenosis. The balloon catheter is subsequently advanced to the pinpointed location by aligning a radiopaque marker of the balloon member with the radiopaque marker on the guide wire corresponding to the location of the stenosis. Because this location is pinpointed relative to the radiopaque marker on the guide wire, additional dye is not needed to assure correct balloon member placement. The balloon member is subsequently inflated, causing the artery wall to stretch and re-establishing an acceptable blood flow through the artery.

To effect an exchange of balloon catheters on the guide wire, the guide wire position is maintained relative to the stenosis while the balloon catheter (uninflated) is withdrawn proximally off of the guide wire. A second balloon catheter bearing a radiopaque marker is then advanced distally over the guide wire until the marker on the catheter is aligned with the marker of the guide wire which defines the location to dilate the stenosis.

BRIEF DESCRIPTION OF THE DRAWINGS

FIG. 1 is a perspective view of an over-the-wire dilatation catheter system in accordance with the present invention.

FIG. 2 is an enlarged sectional view of a distal portion of a guide wire and an over-the-wire balloon dilatation catheter combination of the present invention.

FIG. 3 is a sectional view as taken on line 3—3 of FIG. 2.

FIG. 4 is a sectional view as taken on line 4—4 of FIG. 2.

DETAILED DESCRIPTION OF THE PREFERRED EMBODIMENTS

Catheter 10, as shown in FIGS. 1–4, is an over-the-wire balloon dilatation catheter which includes a manifold 12, a shaft 14, a balloon member 16 and a guide wire 18.

Manifold 12, defining a proximal portion of catheter 10, provides a means for introducing the guide wire 18 and inflation fluid for the balloon member 16 into the shaft 14. A thumb screw 20 is threadably mounted on a proximal end of manifold 12 for use in fixing the position of guide wire 18 relative to the manifold 12, shaft 14 and balloon member 16.

The shaft 14 has an inner tube 22 (see FIG. 2), which is preferably formed from a plastic material such as polyimide, and is attached to the manifold 12 to extend distally therefrom and define a guide wire lumen 24 for the guide wire 18. An inner surface of the inner tube 22 is coated with a lubricious material, such as polytetrafluoroethylene, to facilitate movement of the guide wire 18 therethrough.

The manifold 12 has a dye injection port 26 between the thumb screw 20 and the poximal end of the inner tube 22. The dye injection portion 26 is in fluid communication with the guide wire lumen 24, and is adapted for connection to an inflation device (not shown) to provide fluid (e.g., a radiopaque dye) under pressure to the guide wire lumen 24.

The shaft 14 also has an outer tube 28, attached to the manifold 12, which extends distally therefrom around the inner tube 22. An annular balloon inflation lumen 30 is thus defined between the outer tube 28 and the inner tube 22. The manifold 12 has a balloon inflation port 32 which is in fluid communication with the iteration lumen 30 and is adapted for connection to an inflation device (not shown) to provide fluid under pressure to the balloon member 16 via the inflation lumen 30.

The outer tube 28 is an elongated flexible elastic tube, preferably formed of polyimide. An outer surface of the outer tube 28 has a lubricious coating, such as polytetrafluoroethylene, which provides a slippery surface to said in inserting and removing the catheter 10 into a guide catheter and into a patient's vascular system. At a distal end 34, outer tube 28 has a section of reduced diameter to which a proximal or waist segment 36 of balloon member 16 is attached, preferably by an adhesive seal such as epoxy.

Balloon member 16, which is preferably formed from a polymer material such as polyolefin, has the proximal or waist segment 36, a distensible balloon segment 38 and a small diameter distal segment 40. Distill segment 40 of the balloon member 16 is bounded to a distal end 42 of the inner tube 22, also preferably by an adhesive seal such as epoxy. A radiopaque balloon marker 43 is positioned about the inner tube 22 near a longitudinal center of the balloon member 16 at a distance D from a distal end of the catheter 10.

Guide wire 18 has a proximal solid wire portion 44 which is preferably formed of a high strength steel or other high strength alloy. The solid wire portion 44 has a tapered distal end 46 which is received within and bonded to a proximal end 47 of a coil spring member 48, preferably by a braze bond. Spring member 48 defines a distal protein of the guide wire 18, and is formed from a multiplicity of alternating groups of radiopaque 50 and non-radiopaque 652 spring coils of a high strength steel or other high strength alloy.

Radiopaque markers 56 for the guide wire 18 are formed by sandwiching one or more radiopaque spring coils 50 between nonradiopaque spring coils 52. A radiopaque tip 58 is formed at a distal end of spring member 48 by a plurality of radiopaque spring coils 50. Proximally from the tip 58, adjacent radiopaque markers 56 are longitudinally spaced by the same distance D as is between the distal end of the catheter 10 and its balloon marker 43. The width of the radiopaque markers 56 will depend upon the number of radiopaque spring coils 50 using to form each marker.

In a preferred embodiment, the spring member 48 is 25 cm in length. The distance D between the distal end of catheter 10 and the balloon marker 43 is 1.5 cm. Thus, the radiopaque markers 56 are also separated by 1.5 cm (distance D), with the radiopaque mark 56 (closest to the radiopaque tip 58 being 1.5 cm from its proximal end. The width of each radiopaque marker 56 is preferably 1 mm. The total length of the guide wire is 175 cm.

The basic angioplasty procedure consists of inserting an introducer sheath, or short plastic tube, into a patient's thigh which provides an opening to the femoral artery. A guide catheter (not shown) is then activated through the vascular system and into a position at the ostium of either the left or right coronary artery. The guide character is a hollow tube which services as a channel form outside the patient's body trough which catheter 10 can be advanced to the ostium of a coronary artery.

Prior to inserting the catheter 10 into the artery, the balloon member 16 is positioned on the guide wire 16 adjacent its digital radiopaque tip 58. Once in position, the thumbscrew 10 is tightened to fix the balloon member 16 positioned relative to the guide wire 18. The balloon member 16 and guide wire 18 assembly is then advanced to the ostium of the coronary artery. Using an inflation device which is connected to the dry injection port 26 or the guide catheter, a radiopaque dye is periodically injected into the artery to allow viewing of a stenosis on a fluoroscope. The thumbscrew 20 is loosened to allow the guide wire 18 to be advanced distally across the stenosis while it can be viewed on the fluoroscope. Of course, the guide wire 18 is also viewable on the fluoroscope. The balloon member 16 remains at the ostium of the coronary artery until the guide wire 18 is advanced to a point beyond the stenosis to provide stability to the catheter 10.

Once the guide wire 128 is properly advanced beyond the stenosis, a physician records the position of the stenosis relative to one of the radiopaque markers 56 on the guide wire 18. This recording provides a reference point for the stenosis and thus the periodic injection of dye (which had been necessary to locate the stenosis) can be ceased. The guide wire 128 is then held as still as possible across the stenosis while the balloon member 16 is advanced distally over the guide wire 18. This is done by manually grasping a proximal end of the guide wire 18 outside of the body. The balloon member 16 is advanced until its radiopaque marker 43 is aligned with the stenosis reference mark 56 of the guide wire 18. After the balloon member 16 is properly positioned with respect to the radiopaque marker 56, the thumbscrew 20 on the manifold 12 is tightened to prevent movement of the balloon member 16 relative to the guide wire 18.

The balloon member 16 is subsequently inflated via the inflation lumen 30 so that the distensible balloon segment 38 (shown inflated) expands, exerting pressure radially and outwardly against the stenosis and causing the artery wall to strength. Once the dilution procedure is completed, the balloon member 16 is deflated and removed, re-establishing an acceptable blood flow through the artery.

The radiopaque markers 56 of the guide wire 18 allow the proper placement of balloon 16 across the stenosis without the need for additional continuous or even periodic injections of dye. This is advantageous to the patient because surgical complications arise from the dye injections. Also, this method allows the operation to be performed quickly and efficiently, thereby minimizing radiation exposure to the patient and staff.

The inventive method is also useful in angioplasty procedures which require the use of more than one balloon dilatation catheter. For instance, balloon member 16 of catheter 10 is sometimes too large to fit through the stenosis, or conversely, is so small that upon inflation of the balloon member 16, the stenosis is not sufficiently dilated. In these situations, balloon member 16 must be exchanged for a balloon member of a different size. If the balloon member 16 was too large to fit through the stenosis, a balloon member with a smaller profile must be used. On the other hand, if upon inflation of the balloon member 16 the stenosis was not sufficiently dilated, a balloon member with a larger inflated profile must be inserted to allow a widening of the dilated coronary artery.

In order to exchange balloon member 16 for a different balloon member, the guide wire 18 must be held outside the body (near the femoral artery) so that its position does not move relative to the stenosis. As the guide wire 18 is held in position, the thumbscrew 20 is loosened, allowing the balloon member 16 to be moved proximally along the guide wire 18 and out of the patient's body. The balloon member 16 is continually withdrawn until it is removed from the body and is completely removed from the proximal end of the guide wire 18.

A second dilatation catheter containing a correctly sized balloon member is then placed on the proximal end of the guide wire 18 and moved distally over the guide wire 18. The second dilatation catheter also has a radiopaque marker at a known point of its balloon member (preferably at its midpoint), and the second catheter is advanced along the guide wire 18 until the catheter's marker is aligned as desired with the recorded radiopaque marker 56 on the guide wire 18. The position of the balloon member of the second catheter is then fixed by again tightening the thumbscrew 22. During the entire exchange process, the physical attempts to hold the guide wire 18 steady and in place across the stenosis. If desired, dye may be injected to verify the position of the guide wire 18 and its recorded radiopaque marker 56 or the balloon member once it has been advanced to the recorded marker 56. The second balloon member is then inflated with an inflation medium, applying pressure radially and outwardly to the artery to dilate then stenosis and re-establish an acceptable blood flow through the artery. Upon completion of the angioplasty operation, the second dilatation catheter, guide wire 18, and guide catheter are removed from the patient's thigh.

By providing a guide wire with known spacings between radiopaque markers thereon, and a balloon dilatation catheter having a similar spacing known between its distal end and a radiopaque marker thereon, the positioning of the catheter balloon relative to the guide wire (which is positioned relative to the artery stenosis) is greatly facilitated. For example, if the fifth marker (from a distal end) on the guide wire is aligned across the narrowest point of the stenosis (as detected by fluoroscopy), then the central marker of the balloon is moved over that fifth marker to place the balloon in the most advantageous position for inflation. AS can be appreciated, once a marker on the guide wire is identified as across the stenosis, no further dye injections are necessary to align the catheter balloon, except to possibly recheck the guide wire marker location or to verify that balloon inflation has indeed dilated the artery.

The use of guide wire marker spacings equal to the distance form the distal end of the catheter to its balloon midpoint further assure the physician of balloon position and alignment by providing three reference points as to where the balloon member will be located when it is positioned across the stenosis. The three reference points are the fifth marker which will indicate the location of the midpoint of the balloon member, and the fourth and sixth markers on the guide wire which will indicate the location of the distal and proximal ends of the balloon member respectively. Thus, a physician can determine precisely how much of the stenosis will be contacted by the balloon member when it is inflated.

The balloon dilatation catheter assembly of the present invention thus has considerable advantages over those of the prior art. The invention places a plurality of radiopaque markers at a distal end of the guide wire, which in turn allows a method whereby a balloon member can be positioned properly relative to a stenosis. The radiopaque markers allow for efficient and timely placement of the balloon member without the need to constantly inject additional contrast dye. Consequently, the patient and staff are subject to less radiation exposure and the patient will have fewer complications from dye injections.

Although the present invention has been described with reference to preferred embodiments, workers skilled in the art will recognize that changes may be made in form and detail without departing from the spirit and scope of the invention.

What is claimed is:

1. An intravascular guidewire, comprising:
    an elongate shaft having a proximal portion and a distal portion, the proximal portion comprising a solid wire which tapers distally, the distal portion having distal end portion including a radiopaque coil tip disposed at the distal end portion; and
    a plurality of radiopaque markers disposed on the shaft proximal of the coil tip, the markers defining a plurality of 1.5 cm longitudinal spaces therebetween.

2. The intravascular guidewire of claim 1, wherein the radiopaque markers are 1 mm wide.

* * * * *

UNITED STATES PATENT AND TRADEMARK OFFICE
CERTIFICATE OF CORRECTION

| | | |
|---|---|---|
| PATENT NO. | : 7,033,325 B1 | Page 1 of 1 |
| APPLICATION NO. | : 09/699626 | |
| DATED | : April 25, 2006 | |
| INVENTOR(S) | : Daniel J. Sullivan | |

It is certified that error appears in the above-identified patent and that said Letters Patent is hereby corrected as shown below:

Column 6
Line 54, after "having" insert -- a --.

Signed and Sealed this

Twenty-second Day of August, 2006

JON W. DUDAS
*Director of the United States Patent and Trademark Office*